(12) United States Patent
Watanabe et al.

(10) Patent No.: US 8,433,035 B2
(45) Date of Patent: Apr. 30, 2013

(54) X-RAY FLUORESCENCE ANALYZING METHOD

(75) Inventors: Kenji Watanabe, Takatsuki (JP);
Yoshiyuki Kataoka, Takatsuki (JP);
Yasujiro Yamada, Takatsuki (JP);
Atsushi Morikawa, Takatsuki (JP)

(73) Assignee: Rigaku Corporation, Tokyo (JP)

( * ) Notice: Subject to any disclaimer, the term of this patent is extended or adjusted under 35 U.S.C. 154(b) by 190 days.

(21) Appl. No.: 13/123,121

(22) PCT Filed: Jul. 1, 2010

(86) PCT No.: PCT/JP2010/061250
§ 371 (c)(1),
(2), (4) Date: Apr. 7, 2011

(87) PCT Pub. No.: WO2011/027613
PCT Pub. Date: Mar. 10, 2011

(65) Prior Publication Data
US 2011/0243301 A1 Oct. 6, 2011

(30) Foreign Application Priority Data
Sep. 7, 2009 (JP) ................................. 2009-205822

(51) Int. Cl.
*G01N 23/223* (2006.01)
(52) U.S. Cl.
USPC ............................................. 378/46; 378/44
(58) Field of Classification Search .............. 378/44–50, 378/86–90
See application file for complete search history.

(56) References Cited

U.S. PATENT DOCUMENTS

| 2005/0157843 A1* | 7/2005 | Chen et al. ................. 378/47 |
| 2006/0274882 A1* | 12/2006 | Kawahara et al. ........... 378/45 |
| 2008/0310587 A1* | 12/2008 | Hegeman et al. ............ 378/44 |
| 2009/0116613 A1* | 5/2009 | Kataoka et al. ............. 378/47 |

FOREIGN PATENT DOCUMENTS

| JP | 54-059193 A | 5/1979 |
| JP | 01-214748 A | 8/1989 |
| JP | 10-082749 A | 3/1998 |
| JP | 2002-071590 A | 3/2002 |

(Continued)

OTHER PUBLICATIONS

International Preliminary Report on Patentability PCT/JP2010/061250; Mar. 22, 2012.

(Continued)

*Primary Examiner* — Hoon Song
(74) *Attorney, Agent, or Firm* — Sughrue Mion, PLLC (57) ABSTRACT

An X-ray fluorescence analyzing method includes irradiating a liquid sample (3A) containing hydrogen and at least one element of carbon, oxygen and nitrogen with primary X-rays (2); measuring the intensity F of fluorescent X-rays (4) from each of elements in the sample (3A) and having the atomic number 9 to 20, and the intensity S of scattered X-rays (12) from the sample (3A) caused by continuous X-rays in the primary X-rays; and calculating the concentration of each of the elements, based on the ratio between the measured intensity F, and the measured intensity S. The wavelength of the scattered X-rays (12) is so chosen as to be shorter than that of the fluorescent X-rays (4) and is so set that the measured intensity S and the mass absorption coefficient thereof are inversely proportional to each other within the range of variation of a composition of the sample (3A).

3 Claims, 8 Drawing Sheets

FOREIGN PATENT DOCUMENTS

| | | |
|---|---|---|
| JP | 2007-278965 A | 10/2007 |
| JP | 2008-298679 A | 12/2008 |
| JP | 4629158 B1 | 2/2011 |

OTHER PUBLICATIONS

Bui et al, "Use of Compton scattering in quantitative XRF analysis of stained glass", Applied Radiation and Isotopes International Journal of Radiation Applications and Instrumentation, vol. 40, No. 5, pp. 375-380, Jan. 1, 1989, ISSN: 0883-2889.

Couture, "A reexamination of absorption and enhancement effects in x-ray fluorescence trace element analysis", The American Mineralogist, vol. 81, No. 5-6, pp. 639-650, Jan. 1, 1996.

D.L. Taylor, et al. "Evaluation of an isolated atom model in the use of scattered radiation for internal standardization in x-ray fluorescence analysis" Analytical Chemistry, vol. 43, No. 6, pp. 712-716, May 1, 1971, ISSN: 0003-2700.

European Search Report in Application No. 10813564.1 dated Aug. 8, 2011.

L. Bonizzi et al., "Direct evaluation of 1-3 self-absorption effects in dark matrices by compton scattering measurements", X-Ray Spectrometry, vol. 29, No. 6, pp. 443-448, Nov. 1, 2000, ISSN: 0049-8246.

N.H. Clark et al., "Scattered primary radiation as an internal standard in x-ray emission spectrometry: use in the analysis of copper metallurgical products", X-Ray Spectrometry, vol. 2, No. 2, pp. 47-55, Apr. 1, 1973, ISSN: 0049-8246.

Nielson, K.K., "Matrix corrections for energy dispersive x-ray fluorescence analysis of environmental samples with coherent/incoherent scattered x-rays", Analytical Chemistry, vol. 49, No. 4, pp. 641-648, Apr. 1, 1977, ISSN: 0003-2700.

R. George and M. Schiekel, "Application Limits in using backscattered radiation for Matrix Correction in X-Ray Fluorescence Analysis", Journal of Radioanalytical Chemistry, vol. 79, No. 2, pp. 233-243, 1983.

Yoshiyuki Kataoka, et al., "Doseiren ni Okeru Keiko X-sen Bunseki," Advances in X-ray Chemical Analysis, Nov. 20, 1981, pp. 145-152.

Rigaku Denki Kogyo Kabushiki Kaisha, Oyo Gijutsu Center, (Applied Technology Center), "Keiko X-sen Bunseki Jisshu Tekisuto, (Text Exercise in X-ray Fluorescence Analysis," First print of 4$^{th}$ Ed., Rigaku Denki Kogyo Kabushiki Kaisha, Feb. 1997, pp. 37.

Chinese Patent Application No. 201080002934.9 dated Oct. 15, 2012.

European Communication in Application No. 10813564.1 dated Nov. 21, 2012.

* cited by examiner

X-RAY FLUORESCENCE ANALYZING METHOD

CROSS REFERENCE TO RELATED APPLICATIONS

This application is a National Stage of International Application No. PCT/JP2010/061250 field Jul. 1, 2010, claiming priority based on Japanese Patent Application No. 2009-205822 filed Sep. 7, 2009, the contents of all of which are incorporated herein by reference in their entirely.

BACKGROUND OF THE INVENTION

This application is based on and claims Convention priority to Japanese patent application No. 2009-205822, filed Sep. 7, 2009, the entire disclosure of which is herein incorporated by reference as a part of this application.

The present invention relates to an X-ray fluorescence analyzing method utilizing a so-called scattered X-rays internal standard method.

In the field of X-ray fluorescence analysis, such a method has hitherto been available, in which in determining the content of a metal (an element to be analyzed) contained in, for example, a mineral sample, the ratio between the intensity of fluorescent X-rays, emitted from the element to be analyzed, and the intensity of Compton scattering X-rays of characteristic X-rays of primary X-rays is utilized in order to minimize inter-element effect on the absorption of the fluorescent X-rays emitted from the element to be analyzed. (See the Patent Documents 1 and 2 listed below.) This known method is known as a scattered X-rays internal standard method, in which as internal standard lines the Compton scattering X-rays of the characteristic X-rays of the primary X-rays are utilized. In such case, it has been well known that that the intensity of the Compton scattering X-rays of the characteristic X-rays of the primary X-rays is approximately inversely proportional to the mass absorption coefficient relative to the fluorescent X-rays emitted from the element to be analyzed means that such Compton scattering X-rays are effective as the internal standard line. (See the Non-patent Document 1 listed below.) Also, another method is currently available, in which for the internal standard line, a background in a vicinity of a wavelength of an analytical line, that is, scattered X-rays of a wavelength near the spectrum of the fluorescent X-rays of the element to be analyzed is utilized. (See the Patent Documents 2 and 3 listed below.)

[Patent Document 1] JP Laid-open Patent Publication No. H10-82749 (See Paras. [0037] to [0040])

[Patent Document 2] JP Patent Publication No. 3569734 (See Paras. [0039], [0036] and [0075])

[Patent Document 3] JP Laid-open Patent Publication No. 2008-298679 (See paras. [0001] to [0005] and [0024])

[Non-patent Document 1] Yoshiyuki Kataoka, et al., "Doseiren ni Okeru Keiko X-sen Bunseki", Advances in X-ray Chemical Analysis, 1981, Vol. 13, p. 145-152.

[Non-patent Document 2] Rigaku Denki Kogyo Kabushiki Kaisha, Oyo Gijutsu Center (Applied Technology Center), "Keiko X-sen Bunseki Jisshu Tekisuto (Text for Exercise in X-ray Fluorescence Analysis)", First print of 4-th edition, Rigaku Denki Kogyo Kabushiki Kaisha, February, 1997, p. 37

It has, however, been found that if an attempt is made to determine the concentration (content) of sulfur (an element to be analyzed, which has the atomic number ranging from 9 to 20) contained in, for example, oil relative to a liquid sample such as, for example, oils, organic solvent or aqueous solution, that is, a liquid sample containing, as a principal component, hydrogen and at least one element selected from the group consisting of carbon, oxygen and nitrogen (all of which are a so-called non-measurable element of which fluorescent X-rays cannot be measured as a matter of fact) by the application of the above described prior art technology, the concentration of the element to be analyzed cannot be accurately determined because due to the non-measurable elements contained in quantity in the sample, the internal standard line fail to reflect the composition of the sample accurately.

SUMMARY OF THE INVENTION

In view of the foregoing problems inherent in the prior art methods, the present invention is intended to provide an X-ray fluorescence analyzing method of a kind utilizing the scattered X-rays internal standard method, with which the concentration of the element to be analyzed, which has the atomic number ranging from 9 to 20 and which is contained in a liquid sample containing, as a principal component, hydrogen and at least one element selected from the group consisting of carbon, oxygen and nitrogen, can be calculated accurately.

The inventors of the present invention have found that if the scattered X-rays caused by the continuous X-rays included in the primary X-rays are used as an internal standard line and if the wavelength of the scattered X-rays caused by the continuous X-rays in the primary X-rays is so chosen as to be shorter than the wavelength of the fluorescent X-rays emitted from each of the elements to be analyzed, which has the atomic number ranging from 9 to 20 and is so set that the measured intensity of the scattered X-rays, caused by the continuous X-rays in the primary X-rays, and the mass absorption coefficient thereof are inversely proportional to each other within the range of variation of a composition of the liquid sample, the internal standard line reflects the composition of the sample accurately and the concentration of the element to be analyzed can therefore be accurately calculated. The present invention is based on this finding.

Accordingly, the present invention provides an X-ray fluorescence analyzing method which includes with primary X-rays irradiating a liquid sample containing, as principal components, hydrogen and at least one element selected from the group consisting of carbon, oxygen and nitrogen; measuring the intensity of fluorescent X-rays, emitted from each of elements contained in the liquid sample and having the atomic number ranging from 9 to 20, and the intensity of scattered X-rays from the liquid sample caused by continuous X-rays included in the primary X-rays; and calculating the concentration of each of the elements in the liquid sample, based on the ratio between the measured intensity of the fluorescent X-rays, emitted from each of the elements, and the measured intensity of the scattered X-rays caused by the continuous X-rays in the primary X-rays. In this X-ray fluorescence analyzing method; the wavelength of the scattered X-rays caused by the continuous X-rays in the primary X-rays is so chosen as to be shorter than the wavelength of the fluorescent X-rays emitted from each of the elements and is so set that the measured intensity of the scattered X-rays, caused by the continuous X-rays in the primary X-rays, and the mass absorption coefficient thereof are inversely proportional to each other within the range of variation of a composition of the liquid sample, According to the present invention, the scattered X-rays internal standard method, in which the scattered X-rays caused by the continuous X-rays included in the primary X-rays of the wavelength referred to above is utilized as the internal standard line, is applied to the liquid sample containing, as principal component, hydrogen and at least one element selected from the group consisting of carbon, oxygen and nitrogen, the internal standard line can accurately reflect the composition of the liquid sample and the concentration of the element to be analyzed having the atomic number ranging from 9 to 20 can be calculated accurately.

In the practice of the method of the present invention, the wavelength of the scattered X-rays of the continuous X-rays of the primary X-rays is preferably set to a value within the range of 0.1042 to 0.2505 nm. Also, the wavelength of the scattered X-rays of the continuous X-rays of the primary X-rays, when the element contained in the liquid sample has the atomic number of 15 to 17, is preferably set to a value within the range of 0.123 to 0.193 nm.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF THE PREFERRED EMBODIMENTS

Figure 1:
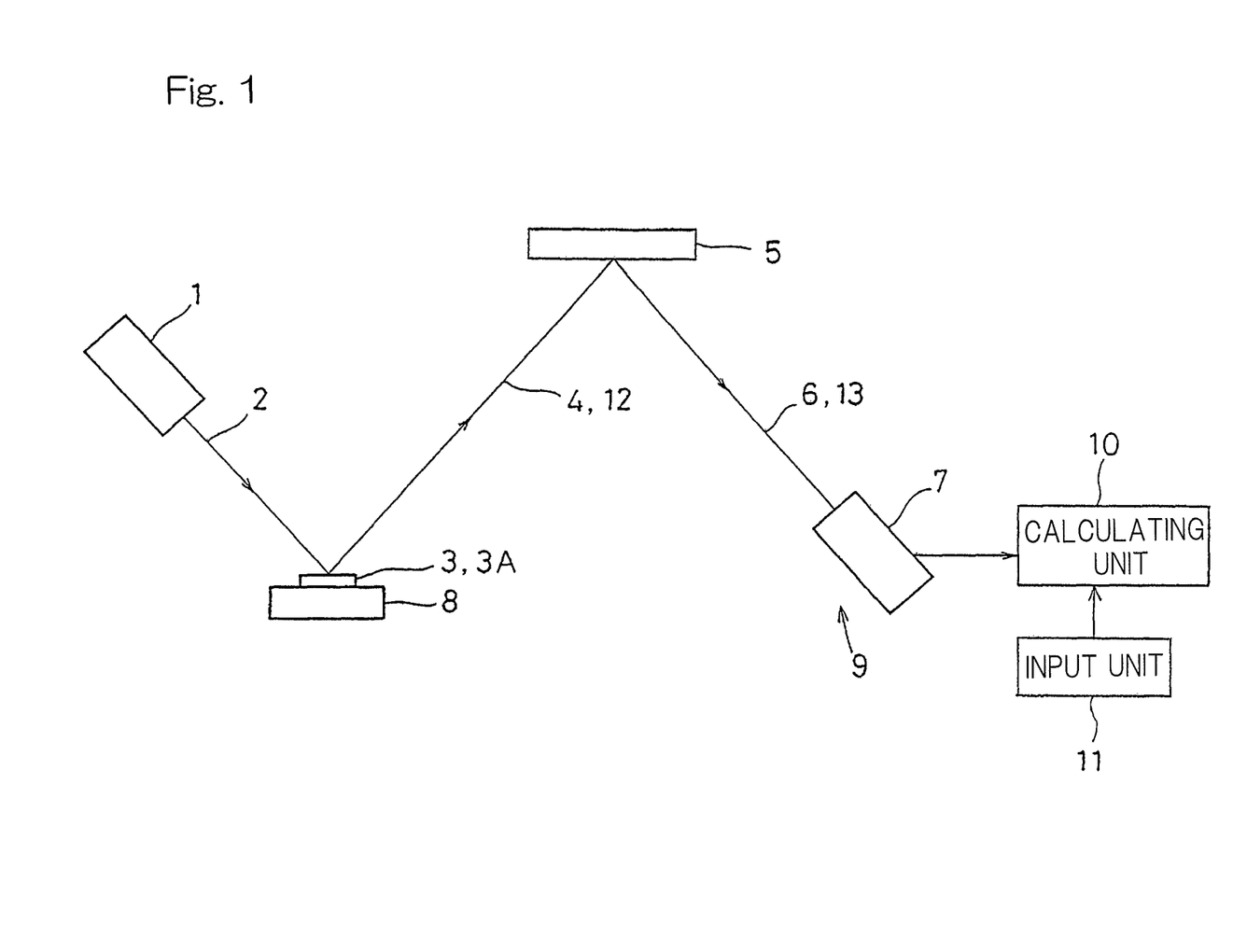
FIG. 1 is a schematic diagram showing an apparatus with which the X-ray fluorescence analyzing method according to a preferred embodiment of the present invention can be practiced.

Before the description of the X-ray fluorescence analyzing method according to a preferred embodiment of the present invention proceeds, an apparatus used in the practice of the X-ray fluorescence analyzing method of the present invention, that is, an X-ray fluorescence spectrometer will be described in detail with particular reference to FIGS. As shown in FIG. 1, the X-ray fluorescence spectrometer includes a sample support 8 on which a sample 3 to be analyzed is placed, an X-ray source 1 such as, for example, an X-ray tube for irradiating the sample 3 with primary X-rays 2, and a detecting unit 9 for measuring respective intensities of fluorescent X-rays 4 and scattered X-rays 12 both emitted from the sample 3. The detecting unit 9 in turn includes a spectroscopic device 5 for monochromating the fluorescent X-rays 4 and the scattered X-rays 12, both emitted from the sample 3 as described above, and a detector 7 for measuring each of the fluorescent X-rays 6 and the scattered X-rays 12, which have been monochromated. It is to be noted that without the spectroscopic device 5 being employed, a detector having a high energy resolution may be employed for the detecting unit. In other words, the X-ray fluorescence spectrometer employed in the practice of the X-ray fluorescence analyzing method according to this embodiment of the present invention may be either a wavelength dispersion type or of an energy dispersion type. Also, radiation of the primary X-rays 2 towards the sample 3 may also be either a top radiation, in which the radiation is made from top, or a bottom radiation, in which the radiation is made from bottom.

The illustrated X-ray fluorescence spectrometer also includes a calculating unit 10 such as, for example, a computer for calculating the concentration of an element contained in the sample 3, based on the intensity, measured by the detecting unit 9, of the fluorescent X-rays 4 which have been emitted from each of the elements contained in the sample 3 and having the atomic number ranging from 9 to 20, and an input unit 11 such as, for example, a mouse, a keyboard and/or a touch panel for inputting an instruction to cause the calculating unit 10 to calculate the concentration of each element, contained in the sample 3, with the use of the scattered X-rays internal standard method and the respective wavelengths of the fluorescent X-rays 4 and the scattered X-rays 12 both to be measured by the detecting unit 9. Although not shown in detail in FIG. 1, an object to be analyzed by the X-ray fluorescence analyzing method according to the embodiment now under discussion is a liquid sample 3A containing, as a principal component, hydrogen and at least one element selected from the group consisting of carbon, oxygen and nitrogen (noting that the composition of the principal component varies depending on the liquid sample 3A), and this liquid sample 3A is hermetically accommodated within any known holder having a window through which the X-rays are permitted to penetrate.

When the instruction to calculate the concentration of each element in the sample 3 by the use of the scattered X-rays internal standard method and the respective wavelengths of the fluorescent X-rays 4 and the scattered X-rays 12, which are to be measured, are inputted to the input unit 11, the calculating unit 10 calculates the concentrations of the elements in the sample 3A, based on the ratio between the intensity, measured by the detecting unit 9, of the fluorescent X-rays 4 emitted from each of the elements contained in the sample 3A and having the atomic number ranging from 9 to 20, and the intensity, also measured by the detecting unit 9, of the scattered X-rays 12 caused by the continuous X-rays included in the primary X-rays. At this moment, setting is made so that the wavelength of the to-be-detected scattered X-rays caused by the continuous X-rays included in the primary X-rays may be shorter than the wavelength of the fluorescent X-rays 4 that will be emitted from each of the elements and, within the range of variation of the composition of the liquid sample 3A, the intensity measured of the scattered X-rays 12 caused by the continuous X-rays included in the primary X-rays and the mass absorption coefficient thereof may be inversely proportional relative to each other, and such setting is inputted. More specifically, the to-be-detected wavelength of the scattered X-rays 13 caused by the continuous X-rays included in the primary X-rays is set to be within the range of 0.1042 to 0.2505 nm and is then inputted.

In other words, the X-ray fluorescence analyzing method according to the embodiment of the present invention is an X-ray fluorescence analyzing method, in which the liquid sample 3A containing, as a principal component, hydrogen ant at least one element selected from the group consisting of carbon, oxygen and nitrogen, is irradiated with the primary X-rays 2, measuring the intensity of the fluorescent X-rays 4, emitted from each of the elements contained in the liquid sample 3A and having the atomic number ranging from 9 to 20, and the intensity of the X-rays 12 which are scattered from the liquid sample 3A as a result of excitation by the continuous X-rays included in the primary X-ray, and calculating the concentration of each of the elements contained in the liquid sample 3A, based on the ratio between the intensity of the fluorescent X-rays 4 emitted from each of the elements contained in the sample 3A and the intensity of the scattered X-rays 12 caused by the continuous X-rays included in the primary X-rays. At this moment, the wavelength of the scattered X-rays 12 caused by the continuous X-rays included in the primary X-rays is so set as to be shorter than the fluorescent X-ray emitted from each of the elements, and so set that within the range of variation of the composition of the liquid sample 3A, the intensity measured of the scattered X-rays 12 caused by the continuous X-rays included in the primary X-rays and the mass absorption coefficient thereof may be inversely proportional relative to each other, specifically, within the range of 0.1042 to 0.2505 nm.

The reason for the use of the scattered X-rays caused by the continuous X-rays included in the primary X-rays of such a wavelength as the internal standard line will now be described subsequently. Where the concentration of the element to be analyzed, which is a light element (which, in the present invention, means an element having the atomic number ranging from 9 to 20) such as, for example, sulfur is to be determined by applying the scattered X-rays internal standard method to the liquid sample such as, for example, oils, organic solvent or aqueous solution which contains, as a principal component, hydrogen and at least one element selected from the group consisting of carbon, oxygen and nitrogen, regarding scattered X-rays as an internal standard line, the proportion of the scattering power between the Compton scattering and the Thomson scattering is important in the first instance.

Considering that the Compton scattering power makes little difference in the case of the elements having the atomic number of 2 or more, but is about twice that exhibited by any other elements having only hydrogen, the Compton scattering X-rays caused by the characteristic X-rays included in the primary X-rays such as, for example, the Compton scattering X-rays of Rh—Kα line cannot be used as the internal standard line where the sample contains a substantial amount of hydrogen. On the other hand, since the scattered X-rays caused by the continuous X-rays in the primary X-rays contain both of the Compton scattering X-rays and the Thomson scattering X-rays, the use as the internal standard line will now be examined. At the outset, the intensity of the scattered X-rays caused by the continuous X-rays when the sample has a finite thickness in terms of the X-rays, it can be expressed by the following formula (1) for simplicity:

[Formula 1]

$$I_{Scat} = k_s \frac{P_{Comp} + P_{Thom}}{\mu_{samp}} (1 - e^{-\mu_{samp} d}) \tag{1}$$

wherein $I_{Scat}$ represents the intensity of the scattered X-rays caused by the continuous X-rays; $\mu_{Samp}$ represents the mass absorption coefficient of the sample, $P_{Comp}$, represents the Compton scattering power of the sample, $P_{Thom}$ represents the Thomson scattering power of the sample, d represents the area density of the sample, and $k_s$ represents the constant.

When the sample has an infinite thickness in terms of the X-rays regarding this wavelength, the following formula (2) can be obtained:

[Formula 2]

$$I_{Scat} = k_s \frac{P_{Comp} + P_{Thom}}{\mu_{samp}} \tag{2}$$

On the other hand, the intensity of the fluorescent X-rays of the same wavelength, when the sample has a finite thickness, can be expressed by the following formula (3) for simplicity:

[Formula 3]

$$I_F = k_F \frac{F_i W_i}{\mu_{samp}} (1 - e^{-\mu_{samp} d}) \tag{3}$$

wherein $I_F$ represents the intensity of the fluorescent X-rays, Fi represents the efficiency of generation of the fluorescent drays, and Wi represents the content of the element to be analyzed.

When the sample has an infinite thickness regarding the fluorescent X-rays of this wavelength, the following formula (4) can be obtained:

[Formula 4]

$$I_F = k_F \frac{F_i W_i}{\mu_{samp}} \quad (4)$$

Accordingly, the ratio between the intensity of the scattered X-rays caused by the continuous X-rays and the intensity of the fluorescent X-rays of the substantially same wavelength can be expressed by the following formula (5) regardless of the thickness of the sample:

[Formula 5]

$$I_R = \frac{I_F}{I_{Scat}} = \frac{k_F}{k_s} \frac{F_i W_i}{P_{camp} + P_{Thom}} \quad (5)$$

As can readily be understood from the formula (5) above, in order to compensate for an influence of the composition of the sample with the use of the scattered X-rays, caused by the continuous X-rays in the primary X-rays, as the internal standard line, the sum ($P_{Comp}+P_{Thom}$) of the Compton scattering power and the Thomson scattering power must be constant regardless of the composition of the sample. Also, as can readily be understood from the formula (2) above, that the sum of the Compton scattering power and the Thomson scattering power is constant regardless of the composition of the sample is equivalent to that regarding the sample having the infinite thickness, the intensity of the scattered X-rays caused by the continuous X-rays is inversely proportional to the mass absorption coefficient of the wavelength of such scattered X-rays.

The proportion of the Compton scattering power and the Thomson scattering power depends on the wavelength of the scattered X-rays caused by the continuous X-rays and the longer the wavelength, the relatively higher the Thomson scattering power. Also, as discussed previously, with respect to the Compton scattering power, hydrogen exhibits about twice that in any other element, but with respect to the Thomson scattering power, hydrogen is conversely extremely small. In view of this, it may be expected that if the wavelength of the scattered X-rays caused by the continuous X-rays is properly chosen, the dependency of the total scattering power, which is the sum of the Compton and Thomson scattering powers, on the composition of the sample can be reduced.

Figure 2:
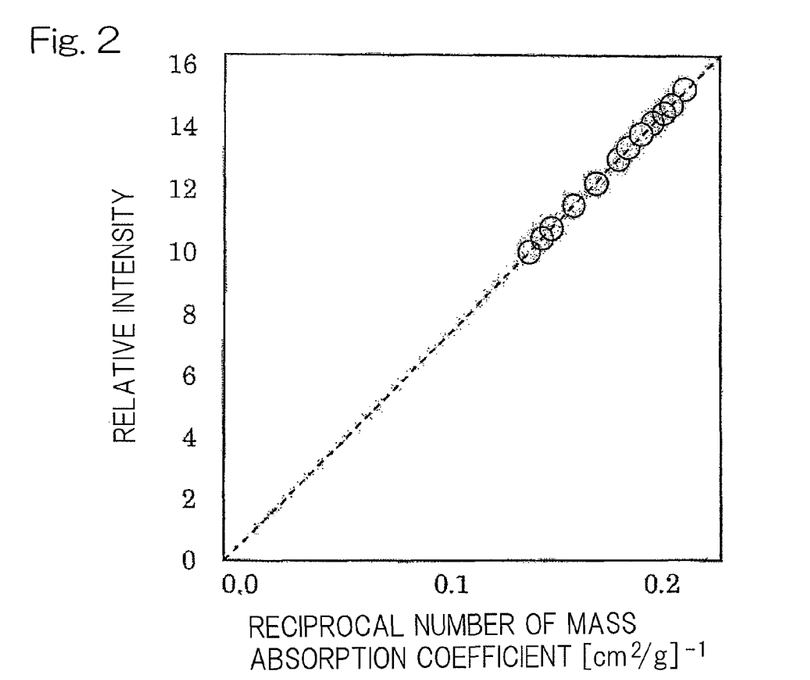
FIG. 2 is a chart showing the relation between the measured intensity and the reciprocal number of the mass absorption coefficient, which is obtained when the scattered X-rays of 0.1607 nm in wavelength caused by the continuous X-rays in the primary X-rays from a liquid sample such as, for example, an oil was examined.
Figure 3:
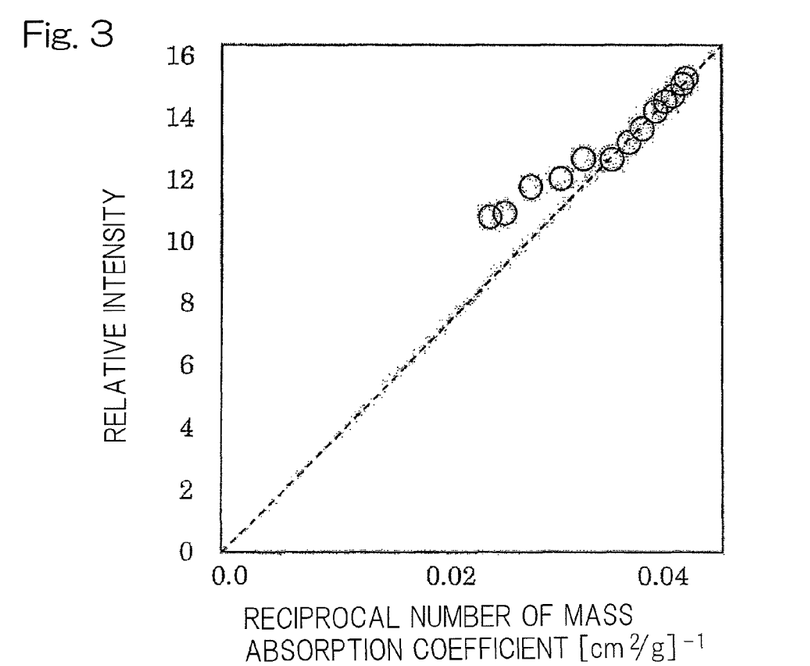
FIG. 3 is a chart showing the relation between the measured intensity and the reciprocal number of the mass absorption coefficient, which is obtained when the scattered X-rays of 0.2776 nm in wavelength caused by the continuous X-rays in the primary X-rays from a liquid sample such as, for example, an oil was examined.

Accordingly, the relation with the mass absorption coefficient has been examined by measuring the intensity of the scattered X-rays caused by the continuous X-rays when the sample used has an infinite thickness. More specifically, using liquid samples of different compositions such as, for example, oils, but containing hydrogen, carbon and oxygen, the relation between the measured intensity (relative intensity) of the scattered X-rays of 0.1607 nm in wavelength, caused by the continuous X-rays, and the reciprocal number of the mass absorption coefficient thereof has been examined, the result of which is shown in FIG. 2. A similar examination has also been made with respect to the scattered X-rays of 0.2776 nm in wavelength caused by the continuous X-rays, the result of which is shown in FIG. 3.

Figure 4:
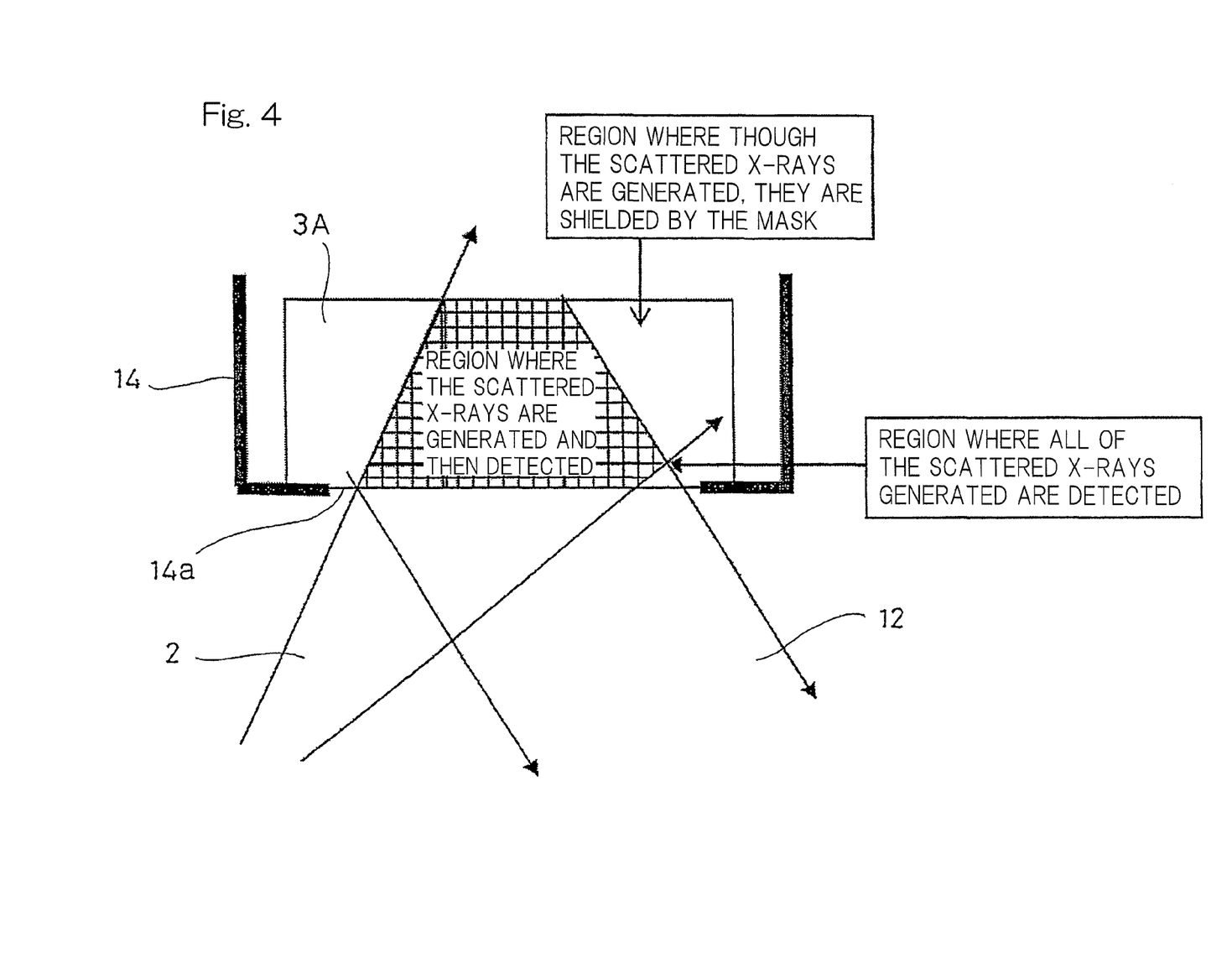
FIG. 4 is a conceptual diagram showing the depth of penetration of the scattered X-rays of the continuous X-rays of the primary X-rays and a range of detection.

Since during the measurement of the sample having the infinite thickness, the scattered X-rays are emitted from a deep region of the sample when excited by the X-rays of a short wavelength and it is shielded by, for example, a mask of a holder before they are detected, it has been confirmed that regarding the optical system of the apparatus used and the amount of the sample (depth of the sample), the scattered X-rays of the above described two wavelengths caused by the continuous X-rays and generated from the sample in a direction of detection could have been detected without being shielded. In this respect, a conceptual diagram of the detecting range and the depth of penetration of the scattered X-rays 12, caused by the continuous X-rays in the primary X-rays, when the liquid sample 3A accommodated within a holder 14, which has its bottom surface formed with an window 14a defined therein for passage of X-rays therethrough, is irradiated from below with the primary X-rays 2, is shown in FIG. 4.

Figure 5A:
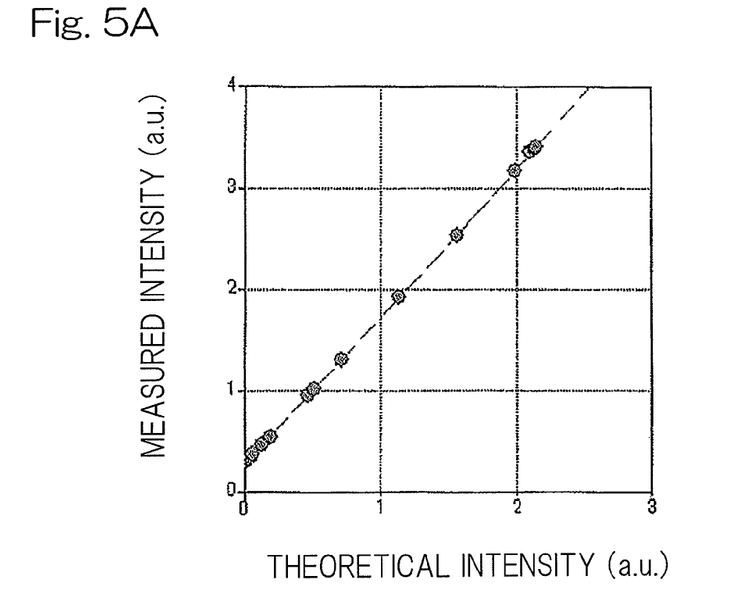
FIG. 5A is a chart showing one example that the measured intensity and the theoretical intensity are in linear relation to each other even when the amount of the sample is increased.
Figure 5B:
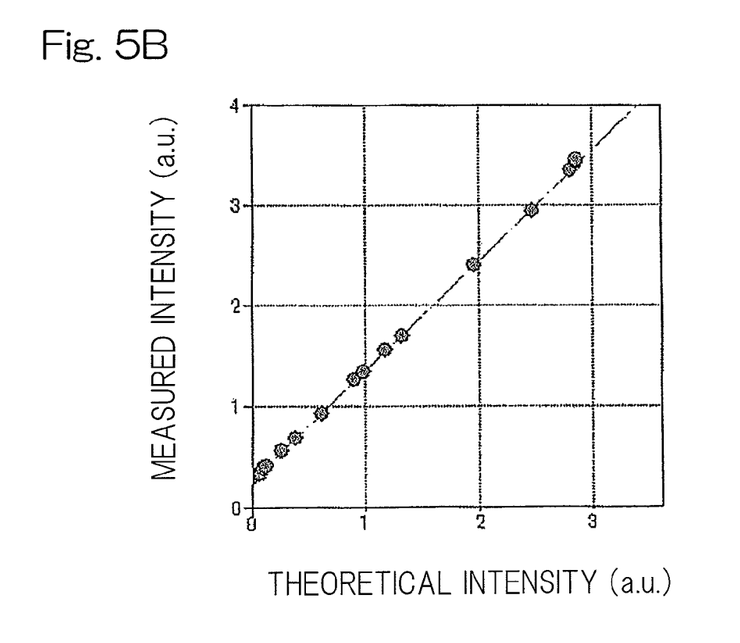
FIG. 5B is a chart showing another example that the measured intensity and the theoretical intensity are in linear relation to each other even when the amount of the sample is increased.
Figure 6:
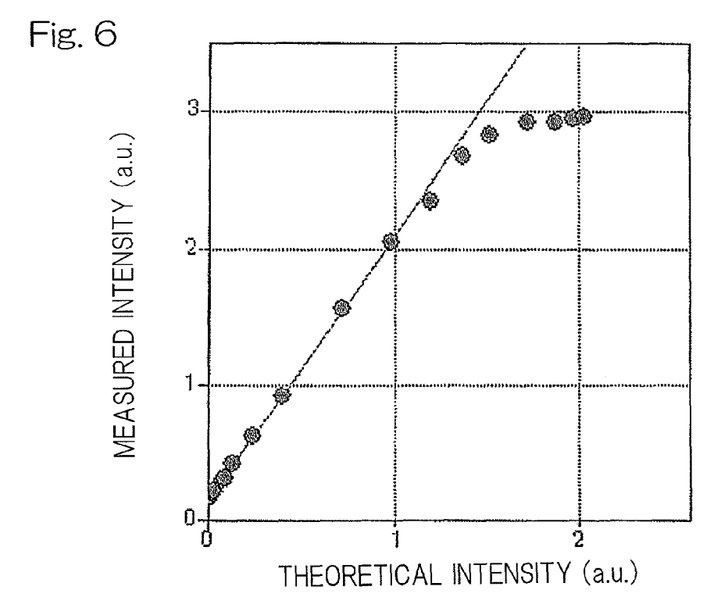
FIG. 6 is a chart showing another example that the measured intensity and the theoretical intensity depart from the linear relation when the amount of the sample is increased.

It is to be noted that when confirmation was to be made, whether or not the intensity measured of the scattered X-rays of the above described two wavelengths, caused by the continuous X-rays, and the theoretical intensity thereof calculated by the fundamental parameter method (FP method) are linearly proportional to each other was examined with the sample amount of the same sample being gradually increased, and, then, the infinite thickness for each sample amount, at which the intensity does no longer increase, was determined. Where by the time the scattered X-rays emitted from the sample is detected, they are shielded by, for example, the mask of the holder, the measured intensity and the theoretical intensity depart from the proportional relation to each other as the sample amount is increased. In the case where polypropylene is used as a sample, an example, in which the measured intensity and the theoretical intensity exhibit the linear proportional relation to each other is shown in FIG. 5A (the wavelength of the scattered X-rays being 0.1344 nm) and FIG. 5B (the wavelength of the scattered X-rays being 0.1607 nm) and a case, in which they depart from the linear proportional relation is shown in FIG. 6 (the wavelength of the scattered X-rays being 0.0653 nm).

As shown in FIG. 2, with respect to the scattered X-rays of 0.1607 nm in wavelength caused by the continuous X-rays, the measured intensity and the reciprocal number of the mass absorption coefficient is in a good proportion to each other, that is, the measured intensity and the mass absorption coefficient are in a good inverse proportion to each other. On the other hand, as shown in FIG. 3, with respect to the scattered X-rays of 0.2776 nm in wavelength caused by the continuous X-rays, no good correlation could have been obtained between the measured intensity and the reciprocal number of the mass absorption coefficient. The wavelength that results in the good correlation as shown in FIG. 2 depends on the optical system of the apparatus, the kind of the liquid sample and the concentration of the element to be analyzed, but where mineral oil, vegetable oil, alcohol and water were used as respective liquid samples and sulfur of a concentration within the range of 0 to 5 mass % was chosen to be an element to be analyzed with the apparatus used during the experiment, a good correlation could have been obtained with respect to the scattered X-rays of 0.1042 to 0.2505 nm in wavelength caused by the continuous X-rays.

Also, the thickness of the sample too is important. In the prior art, in determining the content of a heavy element contained in a plastic material having an finite thickness, the ratio of intensity between the fluorescent X-rays, emitted from the element to be analyzed, and the background in the vicinity of the wavelength thereof is utilized, but the ratio of the intensity thereof is expressed by the following formula (6), which is identical with the formula (5) referred to previously.

[Formula 6]

$$\frac{I_F}{I_{Scat}} = \frac{k_F \frac{FiWi}{\mu_{samp}}(1-e^{-\mu_{samp}d})}{k_s \frac{P_{Comp}+P_{Thom}}{\mu_{samp}}(1-e^{-\mu_{samp}d})} = \frac{k_F}{k_s}\frac{FiWi}{P_{Comp}+P_{Thom}} \quad (6)$$

In other words, since the wavelength of the fluorescent X-rays emitted from the element to be analyzed and the wavelength of the background are substantially identical with each other, it can readily be understood that if the term of the scattering power is constant, an influence of the thickness of the sample and an influence of the composition of the sample can be corrected as shown by the formula (6) above.

However, where the wavelength of the fluorescent X-rays emitted from the element to be analyzed and the wavelength of the scattered X-rays caused by the continuous X-rays in the primary X-rays are different from each other, it can be understood that the influence of the sample thickness and the influence of the sample composition can no longer be corrected as is clear from the following formula (7):

[Formula 7]

$$\frac{I_F}{I_{Scat}} = \frac{k_F \frac{FiWi}{\mu_{samp}^F}(1-e^{-\mu_{samp}^F d})}{k_s \frac{P_{Comp}+P_{Thom}}{\mu_{samp}^S}(1-e^{-\mu_{samp}^S d})} \quad (7)$$

wherein $\mu^F_{Samp}$ represents the mass absorption coefficient of the sample relative to the fluorescent X-rays and $\mu^S_{Samp}$ represents the mass absorption coefficient of the sample relative to the scattered X-rays.

In order to alleviate the foregoing problem, if the amount of the sample results in an infinite thickness thereof as hereinbefore described and all of the fluorescent X-rays, generated from the sample and emitted from the element to be analyzed, and the scattered X-rays caused by the continuous X-rays in the primary X-rays are detected without being shielded, the ratio in intensity between the both can be expressed as shown by the following formula (8):

[Formula 8]

$$\frac{I_F}{I_{Scat}} = \frac{k_F \frac{FiWi}{\mu_{samp}^F}}{k_s \frac{P_{Comp}+P_{Thom}}{\mu_{samp}^S}} \quad (8)$$

As can readily be understood from the formula (8) above, when the scattered X-rays caused by the continuous X-rays in the primary X-rays are used as the internal standard line, the radio of the mass absorption coefficient $\mu^F_{samp}$ relative to the fluorescent X-rays emitted from the element to be analyzed and the mass absorption coefficient $\mu^S_{samp}$ relative to the scattered X-rays caused by the continuous X-rays in the primary X-rays must be constant regardless of whether or not the composition of the sample changes. Accordingly, assuming that the sample contains, as principal components, hydrogen, carbon, nitrogen and oxygen and also contains a minute quantity of sulfur as an element to be analyzed other than the principal components referred to above, the mass absorption coefficient (cm²/g) of each of the principal components relative to the fluorescent X-rays S—Kα line (0.5373 nm in wavelength) of the element to be analyzed, the mass absorption coefficient (cm²/g) of each of the principal components relative to the scattered X-rays (0.1607 nm in wavelength) caused by the continuous X-rays in the primary X-rays, and the ratio between those two mass absorption coefficients under the principal components referred to above are shown in Table 1 below.

TABLE 1

|  | H | C | N | O |
|---|---|---|---|---|
| 0.5373 nm | 0.7925 | 198.997 | 313.288 | 468.299 |
| 0.1607 nm | 0.3833 | 5.1527 | 8.261 | 13.0729 |
| Mass Absorption Coefficient Ratio | 2.0676 | 38.620 | 37.924 | 35.899 |

According to Table 1 above, with the carbon, nitrogen and oxygen, the ratio between those two mass absorption coefficients referred to above attains the substantially same value and only the ratio of the mass absorption coefficient with the hydrogen attains a value considerably different from that with any other elements. In the next place, assuming two different compositions (Composition 1 and Composition 2) consisting of only hydrogen, carbon and oxygen as shown in Table 2, the mass absorption coefficient (cm²/g) of each of the compositions relative to the fluorescent X-rays S—Kα line (0.5373 nm in wavelength) of the element to be analyzed, the mass absorption coefficient (cm²/g) of each of the compositions relative to the scattered X-rays (0.1607 nm in wavelength) caused by the continuous X-rays in the primary X-rays, and the ratio between those two mass absorption coefficients under the compositions referred to above are shown in Table 3 below.

TABLE 2

| Composition | H (mass %) | C (mass %) | O (mass %) |
|---|---|---|---|
| Composition 1 | 14.37 | 85.63 | 0.00 |
| Composition 2 | 4.20 | 62.50 | 33.30 |

TABLE 3

|  | Composition 1 | Composition 2 |
|---|---|---|
| 0.5373 nm | 170.5 | 280.7 |
| 0.1607 nm | 4.47 | 7.59 |
| Ratio | 38.2 | 37.0 |

As can readily be understood from Table 3 above, the radio between the mass absorption coefficient relative to the fluorescent X-rays emitted from the element to be analyzed and the mass absorption coefficient relative to the scattered X-rays caused by the continuous X-rays in the primary X-rays is close to constant regardless of whether or not the composition changes. This is because as shown in Table 1, though the ratio between those two mass absorption coefficients of hydrogen differs considerably from the ratio of any other principal component, the absolute value of the mass absorption coefficient of hydrogen is sufficiently smaller than the absolute value of the mass absorption coefficient of any other principal component and, therefore, the influence brought about by the mass absorption coefficient of hydrogen on the mass absorption coefficient of the composition in its entirety becomes sufficiently minimized.

Figure 7:
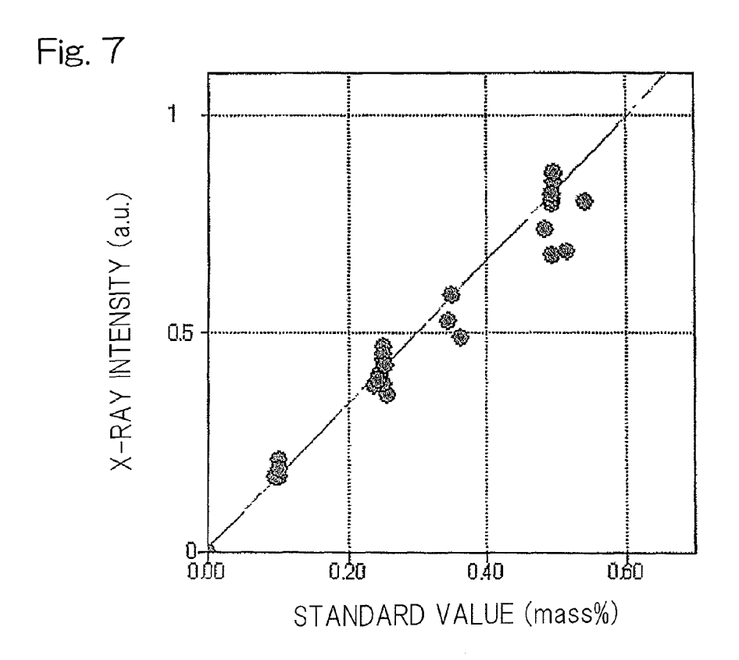
FIG. 7 is a chart showing the calibration curve exhibited by sulfur contained in a liquid sample such as, for example, an oil or organic solvent when no correction is specifically made.
Figure 8:
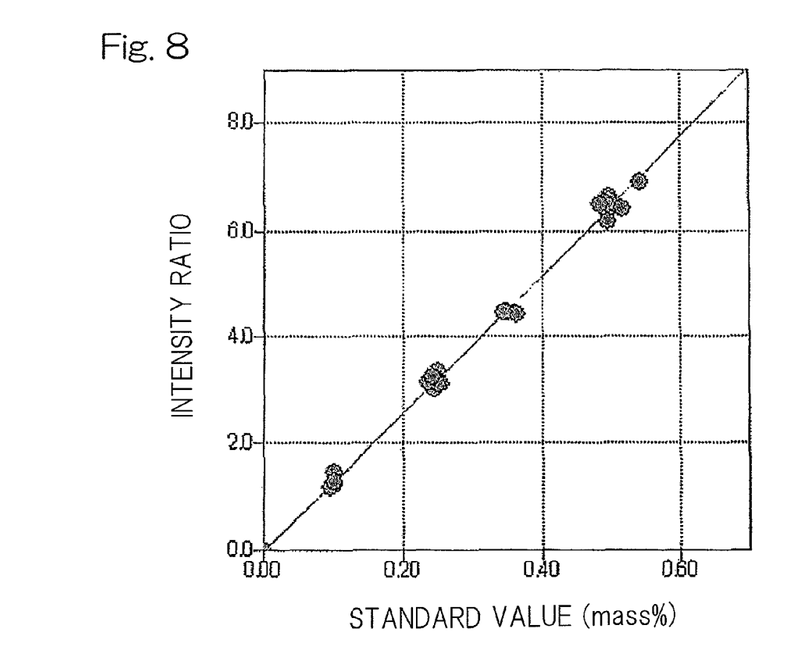
FIG. 8 is a chart showing the calibration curve exhibited by sulfur contained in a liquid sample such as, for example, an oil or organic solvent when the scattered X-rays internal standard correction is made in accordance with the present invention.

Using a liquid paraffin, tetrahydronaphthalene, decahydronaphthalene, decane, xylene, turpentine oil, decanol, pentanol, hexanol, linolic acid and oleic acid as respective liquid samples and, also, sulfur of a concentration within the range of 0 to 0.54 mass % as an element to be analyzed, and while the calibration curve exhibited particularly when no correction was made is shown in FIG. 7, the calibration curve, exhibited when the scattered X-rays internal standard correction is carried out in accordance with the present invention when the scattered X-rays of 0.1607 nm in wavelength caused by the continuous X-rays in the primary X-rays was used as the internal standard line, is shown in FIG. 8. While the calibration curve shown in FIG. 7 is unacceptable because it was considerably affected by the sample composition, the calibration curve shown in FIG. 8 reveals that the influence brought about by the sample composition has been properly removed owning to the correction. In other words, unlike the case, in which in determining the content of a heavy element in a plastic material having a finite thickness with the use of the conventional technique, the background in the vicinity of the wavelength of the fluorescent X-rays emitted from the element to be analyzed is used as the internal standard line, the scattered X-rays caused by the continuous X-rays of a wavelength shorter than the wavelength of the fluorescent X-rays (S—Kα line of 0.5373 nm in wavelength in this instance) emitted from the element to be analyzed becomes effective as the internal standard line in the determination of the concentration of the element to be analyzed, which is contained in the liquid sample containing, as principal components hydrogen and at least one element selected from the group consisting of carbon, oxygen and nitrogen and which has the atomic number ranging from 9 to 20.

By the way, where the liquid sample is a lubricant oil, the sample contains a relatively high concentration of additive elements and depending on the kind of the lubricant oil, the base oil differs. By way of example, assuming that a lubricant oil containing calcium is a sample, the mass absorption coefficient ($cm^2/g$) of the calcium relative to the fluorescent X-rays S—Kα line (0.5373 nm in wavelength) exhibited by the element to be analyzed, the mass absorption coefficient ($cm^2/g$) of the calcium relative to the scattered X-rays (0.1607 nm in wavelength) caused by the continuous X-rays included in the primary X-rays, and the ratio between those two mass absorption coefficients are shown in Table 4 below: It is to be noted that the absorption edge of Ca—K is 0.307 nm and exists between the wavelength of the fluorescent X-rays S—Kα line exhibited by the element to be analyzed and the wavelength of the scattered X-rays caused by the continuous X-rays in the primary X-rays as the internal standard line.

TABLE 4

| | Ca |
|---|---|
| 0.5373 nm | 534.24 |
| 0.1607 nm | 193.81 |
| Absorption Coefficient Ratio | 2.756 |

Not only does the ratio between those two mass absorption coefficients exhibited with calcium differ considerably from the ratio exhibited with the carbon, nitrogen and oxygen shown in Table 1, but also unlike the case with the hydrogen, the absolute value of the mass absorption coefficient exhibited with calcium is greater than the absolute value of the mass absorption coefficient exhibited with the carbon, nitrogen and oxygen, and, therefore, any influence, which the mass absorption coefficient exhibited with calcium may bring about on the mass absorption coefficient exhibited with the sample as a whole cannot be negligible.

As hereinabove discussed, where the element having the absorption edge lying between the wavelength of the fluorescent X-rays emitted from the element to be analyzed and the wavelength of the scattered X-rays caused by the continuous X-rays in the primary X-rays as the internal standard line is contained in the sample, a so-called matrix correction can be carried out following the formula (9) below, by using such element in a matrix correction factor and measuring the intensity of the fluorescent X-rays from such element:

[Formula 9]

$$W_i = \left(A \frac{I_F}{I_{Scat}} + B\right)\left(1 + \sum \alpha_j W_j\right) \quad (9)$$

wherein $W_i$ represents the content of the element to be analyzed, A and B represents calibration curve constants, $\alpha_j$ represents the matrix correction constant, and $W_j$ represents the content of the element in a matrix correction factor.

The matrix correction constant $\alpha_j$ shown in the formula (9) may be determined experimentally by a regression calculation after measurement has been made of a standard sample of a known composition, but containing the element to be analyzed and the element in a matrix correction factor or, alternatively, by calculating the theoretical intensity of the scattered X-rays and the fluorescent X-rays according to the FP method. In the latter case, the method will be a sort of the semi-fundamental parameter method (SFP method) of the calibration curve technique.

Figure 9:
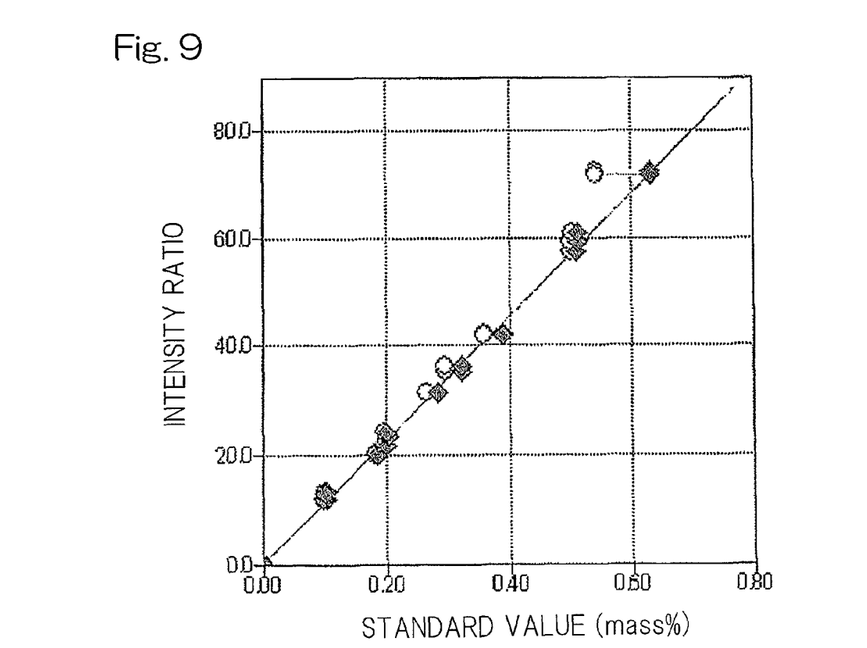
FIG. 9 is a chart showing the calibration curve exhibited by sulfur contained in a liquid sample such as, for example, a lubricant oil when the scattered X-rays internal standard correction is made in accordance with the present invention with matrix correction by calcium as a correcting element.

The calibration curve, exhibited when the scattered X-rays internal standard correction in accordance with the present invention has been made using a lubricant oil and an oil, which is not a lubricant oil, as respective liquid samples, and, also, sulfur as an element to be analyzed and calcium as an element in a matrix correction factor and, also, using the scattered X-rays of 0.1607 nm in wavelength caused by the continuous X-rays in the primary X-rays as the internal standard line, is shown in FIG. 9. The calibration curve shown in FIG. 9 makes it clear that the influence which may be brought about by the sample composition could have been properly removed by the correction. It is to be noted that although nothing was made during the preparation of the calibration curve shown in FIG. 9, even when the sample contains an element having an absorption edge at a site outside a site between the respective wavelengths of the fluorescent X-rays emitted from the element to be analyzed and the wavelength of the scattered X-rays caused by the continuous X-rays in the primary X-rays as the internal standard line, for the purpose of a further accurate analysis it is desirable to use such element as an element in a matrix correction factor, to measure the intensity of the fluorescent X-rays thereof and, then, to perform the matrix correction according to the formula (9) referred to above.

According to the method of the present invention as hereinabove fully described, since the scattered X-rays internal standard method, in which the scattered X-rays 12 caused by the continuous X-rays included in the primary X-rays, of a wavelength set to a value as hereinbefore described as the internal standard line is applied to the liquid sample 3A containing, as principal components, hydrogen and at least one element selected from the group consisting of carbon, oxygen and nitrogen, the internal standard line can accurately reflect the composition of the liquid sample 3A and the concentration of the element to be analyzed, which has the atomic number ranging from 9 to 20, can be calculated accurately.

Figure 10:
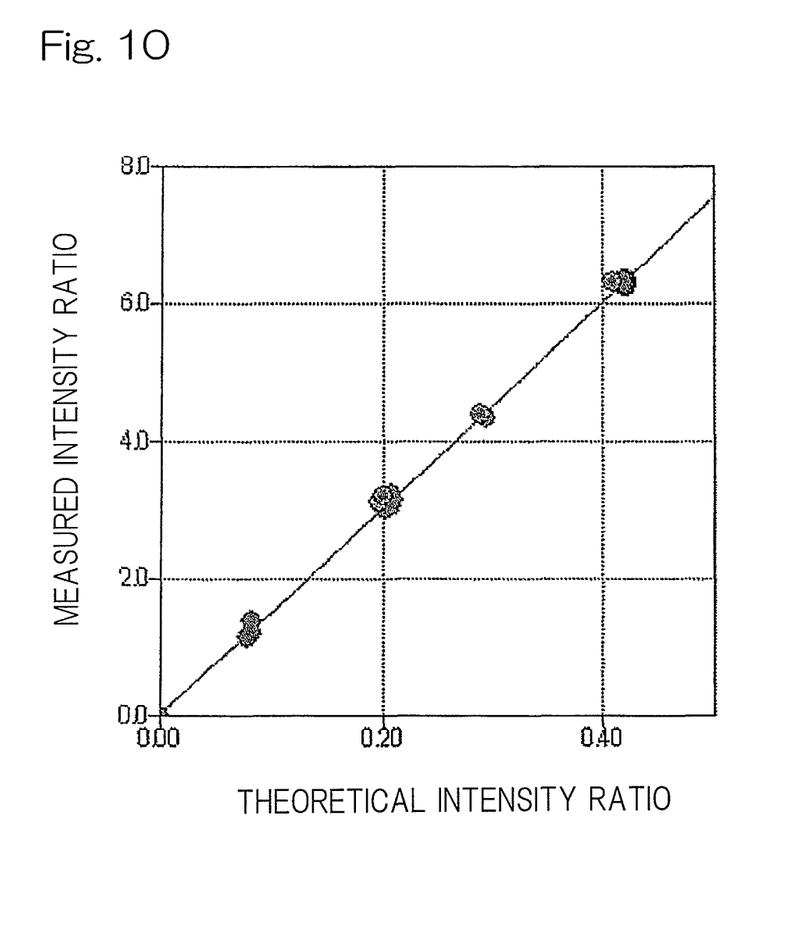
FIG. 10 is a chart showing an apparatus sensitivity curve exhibited by sulfur, which is obtained when the scattered X-rays internal standard correction according to the present invention is effected to a variety of oils used as liquid samples.

It is to be noted that although in the foregoing description, the embodiment of the present invention, in which the calibration curve method is utilized, has been described, the present invention can be equally applied to the X-ray fluorescence analyzing method in which the fundamental parameter method is utilized and even in this case, functions and effects similar to those described hereinbefore can be equally obtained. For example, the desirable apparatus sensitivity curve, which was obtained in connection with the ratio between the intensity of the fluorescent X-rays S—Kα line (0.5373 nm in wavelength) exhibited by the element to be analyzed and the intensity of the scattered X-rays (0.1344 nm in wavelength) caused by the continuous X-rays in the primary X-rays as the internal standard line, when the measurement was carried out with various oils used as liquid samples, is shown in FIG. 10. It will readily be understood that even in the X-ray fluorescence analyzing method utilizing the fundamental parameter method, the scattered X-rays internal standard correction according to the present invention is effective to properly remove the influence brought about by the sample composition.

Figure 11:
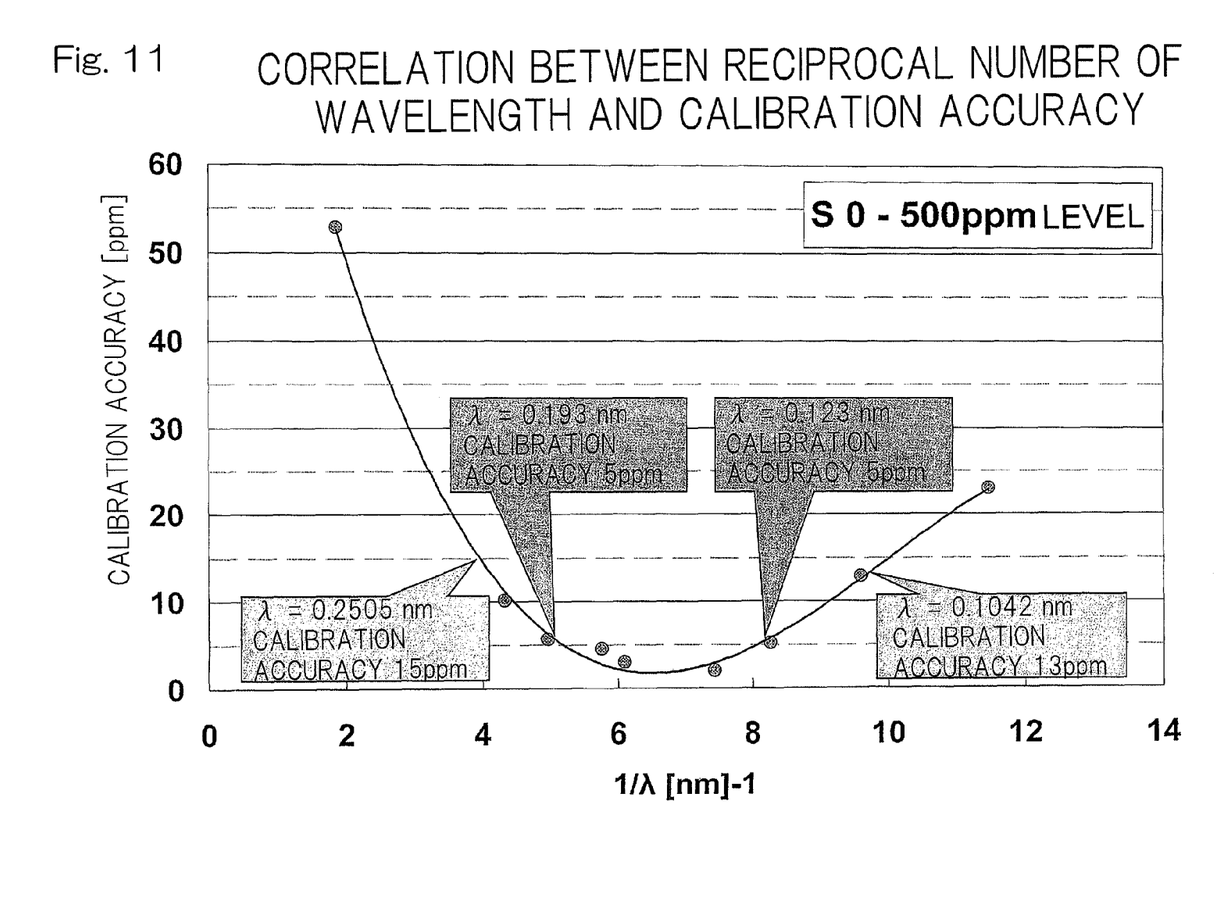
FIG. 11 is a chart showing the correlation between reciprocal number $1/\lambda$ (1/nm) of the wavelength of the scattered X-rays, caused by the continuous X-rays in the primary X-rays and used as the internal standard line, and calibration accuracy (ppm), which are exhibited in the calibration curve of sulfur of 500 ppm in level prepared by effecting the scattered X-rays internal standard correction according to the present invention.

The correlation between the calibration accuracy (ppm) and the reciprocal number $1/\lambda$ (1/nm) of the wavelength of the scattered X-rays used as the internal standard line, caused by the continuous X-rays in the primary X-rays, which is exhibited in the calibration curve of sulfur (atomic number being 16) of 500 ppm level prepared by effecting the scattered X-rays internal standard correction according to the present invention, is shown in FIG. 11. According to the chart shown in FIG. 11, the calibration accuracy is 15 ppm or smaller at a wavelength within the range of 0.1042 to 0.2505 nm of the scattered X-rays caused by the continuous X-rays in the primary X-rays and, based on this, in the X-ray fluorescence analyzing method according to the foregoing embodiment of the present invention, the wavelength of the scattered X-rays caused by the continuous X-rays in the primary X-rays is chosen to be a value within the range of 0.1042 to 0.2505 nm relative to the element in the liquid sample, having the atomic number ranging from 9 to 20 with sulfur taken as a center. Also, the chart of FIG. 11 makes it clear that since the calibration accuracy is 5 ppm or smaller at a wavelength within the range of 0.123 to 0.193 nm of the wavelength of the scattered X-rays caused by the continuous X-rays in the primary X-rays, the wavelength of the scattered X-rays caused by the continuous X-rays in the primary X-rays is preferably set to a value within the range of 0.123 to 0.193 nm relative to the element in the liquid sample, having the atomic number ranging from 15 to 17 with sulfur taken as a center.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1: X-ray source
2: Primary X-rays
3: Sample
3A: Liquid sample
4: Fluorescent X-rays
9: Detecting unit
10: Calculating unit
11: Input unit
12: Scattered X-rays caused by continuous X-rays included in primary X-rays

What is claimed is:

1. An X-ray fluorescence analyzing method which comprises:
    with primary X-rays irradiating a liquid sample containing, as principal components, hydrogen and at least one element selected from the group consisting of carbon, oxygen and nitrogen;
    utilizing, as an internal standard line, scattered X-rays caused by continuous X-rays included in the primary X-rays for a scattered X-rays internal standard method;
    measuring the intensity of fluorescent X-rays, emitted from each of elements contained in the liquid sample and having the atomic number ranging from 9 to 20, and the intensity of scattered X-rays from the liquid sample caused by continuous X-rays in the primary X-rays and utilized as the internal standard line; and
    calculating the concentration of each of the elements in the liquid sample, based on the ratio between the measured intensity of the fluorescent X-rays, emitted from each of the elements, and the measured intensity of the scattered X-rays caused by the continuous X-rays in the primary X-rays and utilized as the internal standard line;
    wherein the wavelength of the scattered X-rays caused by the continuous X-rays in the primary X-rays and utilized as the internal standard line is so chosen as to be shorter than the wavelength of the fluorescent X-rays emitted from each of the elements and is so set that the measured intensity of the scattered X-rays, caused by the continuous X-rays in the primary X-rays and utilized as the internal standard line, and the mass absorption coefficient thereof are inversely proportional to each other within the range of variation of a composition of the liquid sample, assuming that the sample has an infinite thickness.

2. The X-ray fluorescence analyzing method as claimed in claim 1, in which the wavelength of the scattered X-rays caused by the continuous X-rays in the primary X-rays and utilized as the internal standard line is chosen to be within the range of 0.1042 to 0.2505 nm.

3. The X-ray fluorescence analyzing method as claimed in claim 1, in which the wavelength of the scattered X-rays caused by the continuous X-rays in the primary X-rays and utilized as the internal standard line is chosen to be within the range of 0.123 to 0.193 nm relative to the element contained in the liquid sample and having the atomic number ranging from 15 to 17.

* * * * *